United States Patent
Minden et al.

(10) Patent No.: US 10,362,237 B2
(45) Date of Patent: Jul. 23, 2019

(54) STRUCTURED ILLUMINATION SYSTEM FOR INCREASED DYNAMIC RANGE IN QUANTITATIVE IMAGING

(71) Applicants: Jonathan Minden, Pittsburgh, PA (US); Frederick Lanni, Pittsburgh, PA (US); Phu T Van, Seattle, WA (US); Carnegie Mellon University, Pittsburgh, PA (US)

(72) Inventors: Jonathan Minden, Pittsburgh, PA (US); Frederick Lanni, Pittsburgh, PA (US); Phu T Van, Seattle, WA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 15/576,570

(22) PCT Filed: May 26, 2016

(86) PCT No.: PCT/US2016/034325
§ 371 (c)(1),
(2) Date: Nov. 22, 2017

(87) PCT Pub. No.: WO2016/191557
PCT Pub. Date: Dec. 1, 2016

(65) Prior Publication Data
US 2018/0167542 A1 Jun. 14, 2018

Related U.S. Application Data

(60) Provisional application No. 62/230,044, filed on May 26, 2015.

(51) Int. Cl.
| | | |
|---|---|---|
| H04N 5/235 | (2006.01) |
| G03B 7/08 | (2014.01) |
| G03B 15/02 | (2006.01) |
| G01N 21/64 | (2006.01) |
| G01N 27/447 | (2006.01) |

(Continued)

(52) U.S. Cl.
CPC ............ *H04N 5/2354* (2013.01); *C07K 1/26* (2013.01); *G01N 21/6456* (2013.01); *G01N 27/44747* (2013.01); *G03B 7/08* (2013.01); *G03B 7/093* (2013.01); *G03B 15/02* (2013.01); *H04N 5/2355* (2013.01); *H04N 5/2356* (2013.01); *G01N 2201/06113* (2013.01); *G03B 2215/0596* (2013.01)

(58) Field of Classification Search
None
See application file for complete search history.

(56) References Cited

U.S. PATENT DOCUMENTS 5,541,705 A * 7/1996 Kan .................. G03B 7/28
396/233
2006/0226375 A1* 10/2006 Maruo ................ G01N 21/645
250/458.1

(Continued)

*Primary Examiner* — William B Perkey

(57) ABSTRACT

The present disclosure provides systems and methods for the measurement of signal intensity across a large dynamic range. The systems disclosed herein employ an iterative image collection strategy that utilizes structured illumination to achieve greater than 1,000,000-fold dynamic range measurements, representing a dramatic improvement over the prior art.

20 Claims, 8 Drawing Sheets

(51) Int. Cl.
*C07K 1/26* (2006.01)
*G03B 7/093* (2006.01)

(56) References Cited

U.S. PATENT DOCUMENTS

| | | | |
|---|---|---|---|
| 2007/0132998 A1* | 6/2007 | Tang | G01N 21/6458 |
| | | | 356/417 |
| 2008/0007645 A1* | 1/2008 | McCutchen | H04N 5/238 |
| | | | 348/360 |
| 2011/0134280 A1* | 6/2011 | Chou | H04N 5/2351 |
| | | | 348/234 |
| 2011/0157419 A1* | 6/2011 | Nayar | H04N 5/235 |
| | | | 348/229.1 |
| 2016/0112622 A1* | 4/2016 | Gressum | G03B 15/02 |
| | | | 348/370 |
| 2016/0164261 A1* | 6/2016 | Warren | H04N 5/2354 |
| | | | 348/164 |
| 2016/0296112 A1* | 10/2016 | Fletcher | A61B 3/14 |
| 2016/0316153 A1* | 10/2016 | Grauer | H01L 27/14621 |
| 2016/0352993 A1* | 12/2016 | Gerasimow | H04N 5/2354 |
| 2017/0180622 A1* | 6/2017 | Zabatani | H04N 5/2351 |
| 2018/0167542 A1* | 6/2018 | Minden | H04N 5/2355 |

* cited by examiner

STRUCTURED ILLUMINATION SYSTEM FOR INCREASED DYNAMIC RANGE IN QUANTITATIVE IMAGING

CROSS-REFERENCE TO RELATED APPLICATIONS

This application claims the benefit under 35 U.S.C. § 119(e) of the earlier filing date of U.S. Provisional Patent Application No. 62/230,044 filed on May 26, 2015.

STATEMENT OF GOVERNMENT SUPPORT

This invention was made with government support under DBI1063236 awarded by the National Science Foundation. The government has certain rights in the invention.

BACKGROUND OF THE INVENTION

1. Field of the Invention

The present invention relates generally to image collection. More particularly, the present invention is directed to image collection methods and systems that may achieve dynamic range sensitivities of up to 1,000,000 fold.

2. Description of the Background

A major challenge for comparative proteomics is the large range of protein concentration in complex biological samples. For example, in the budding yeast *Saccharomyces cerevisiae*, proteins have been measured to range from about ten copies per cell to ~1.5 million copies per cell, reflecting an approximately 150,000-fold concentration range. These large concentration ranges pose an important hurdle for unbiased, proteome-wide evaluations that seek to identify changes in protein concentration and post-translational modification of all cellular proteins.

Current comparative proteomics strategies fall into two general categories referred to as "peptide-centric" and "protein-centric." The peptide-centric approach relies on mass spectrometry (MS) for protein quantification by the detection of peptides generated by enzymatic digestion of protein samples. This commonly used method employs liquid chromatography followed by tandem MS (LC-MS/MS) to detect peptides over a ~1,000-fold concentration range. Selected Reaction Monitoring (SRM) is an MS refinement that utilizes a list of user-defined proteins to direct the search and quantification of those selected peptides and their fragmentation products. While SRM is a powerful quantification tool, it requires a priori knowledge of which specific fragmentation reactions may occur. For this reason, SRM cannot be used effectively for unbiased, comparative proteome studies.

The protein-centric approach divides comparative proteomics method into two main tasks: (1) separation of intact proteins by 2D gel electrophoresis (2DE) followed by quantitative protein detection; and (2) identifying proteins of interest by MS. Difference Gel Electrophoresis (DIGE) is a commonly used method for comparing different fluorescently tagged proteome preparations. Standard 2DE gels are capable of resolving ~2000 protein spots per gel; large-format 2DE gels can resolve more than 10,000 spots. 2DE gels have very high resolution (capable of resolving protein spots that differ by 0.001 pH units) and are also extremely sensitive, able to detect down to <1 ng of protein per spot. The combination of high sensitivity and effective spatial separation makes 2DE gels well-suited not only for detecting changes in protein abundance, but also for distinguishing subtle changes in proteins, such as different protein isoforms and post-translational modifications.

Quantification of protein spots is typically performed either with scientific-grade cameras using full-field illumination or laser scanning imagers. In the resultant images, highly abundant proteins appear as large, bright spots; less abundant proteins appear as small, dim spots. The development of DIGE allowed the running and thus comparison of two or three samples in the same gel using mass- and charge-matched cyanine-based, fluorescent dyes. Since the samples are subjected to the same electrophoretic forces simultaneously, inter-gel variability is eliminated. DIGE allows for the detection of very small differences in protein abundance, charge, or mass (as low as ±15%). DIGE has been used in many studies to obtain comprehensive protein "snapshots" of complex samples at a particular point in time. Previous studies estimated that full-field and laser scanning imaging of 2D DIGE gels has a dynamic range of about 10,000-fold, defined as the ratio between highest and lowest fluorescent intensity of detected spots. While this reflects the ability to collect extensive intensity-based data, this performance still falls short of the dynamic range required to conduct whole-cell proteome studies.

A major limitation to detecting the full concentration range of cellular proteins in 2DE gels is the dynamic range of the imaging device as utilized in the prior art. Prior art systems typically evaluate proteins in a 2DE gel by employing fluorescence imagers that use full-field illumination and Charged-Coupled Device (CCD) cameras. Under these circumstances, protein spots having high levels of protein are highly fluorescent, and thus require relatively short exposures. Low abundance protein spots require longer exposures to obtain a detectable signal. Further complicating analysis, 2DE gels often have high abundance proteins in close proximity to low abundance proteins.

Exposure times required to detect low abundance proteins typically result in pixel saturation in portions of the image that reflect the fluorescent signals arising from high abundance proteins. Saturated pixels all report the detector's maximum detection value, regardless of their true intensity, thus leading to inaccurate intensity values for measurements of high abundance protein. The detectors employed for fluorescence imaging usually utilize 16-bit CCD cameras or photomultipliers, thus saturating at 65,535 ($2^{16}-1$) counts. The detection range of such systems is further reduced, however, by the noise characteristics of electronic detectors, the variability of biological samples, and background fluorescence signals. As a result, the current detection-range limit of fluorescent gel imaging systems is about 10,000-fold. This intensity detection range is inadequate to capture the actual intensity of signal produced by proteins in a 2DE gel. Overcoming this detector saturation limit is essential for obtaining high dynamic range gel images, and thus accurate measurements of protein fluorescence.

Similar difficulties resulting from inadequate dynamic range of detection systems are in encountered in numerous other circumstances. For example, measurement of the intensity of immunohistochemically stained tissue may also result in saturation of the measurement system. Similarly, activity-dependent dyes (e.g., calcium-sensitive dyes) may also generate fluorescent signals that saturate the detection device. At the same time, the sample may produce low-intensity signals that reflect relevant information. Similar limitations are also present in scene imaging, robotic vision, and microscopy applications. In each case, saturation results in an inaccurate measurement of the true signals being generated from the sample, while low-intensity sections of the image are inadequately assessed.

Thus, there has been a long-standing need in the scientific community for detection system that have a sufficiently broad dynamic range to accurately capture the true breadth of signals generated from an experimental sample, such as, but not limited to, 2DE gels. The present invention addresses this need.

SUMMARY OF THE INVENTION

The present invention addresses the limitations currently existing within the art and provides systems and methods capable of accurately measuring signal intensity of a sample across a very wide dynamic range using an iterative image collection process. In some implementations of the methods and systems of the present invention, a dynamic range of greater than 1,000,000-fold may be achieved.

The methods of the present invention may be practiced with an illumination system that includes a light source, an electronic image collection device, a computer system running a software package, and a sample. In some implementations, the sample is a biological sample and, in some instances, a 2DE protein gel or a 1DE protein gel in which the proteins are labeled with a fluorescent marker. In those circumstances, the illumination system may also include a microscope that is useful for achieving appropriate magnification, as well as filters useful for adjusting the wavelength of the light from the light source to appropriately excite and measure the emission from the fluorescent proteins in the biological sample. In some implementations, the light source is an LCD projector or a scanning laser illumination system. In some implementations, the electronic image collection device is a CCD camera or a photomultiplier tube coupled with a laser scanning head.

The present invention may be practiced in the following manner. The light source capable of being controlled on a pixel-by-pixel basis is used to illuminate the sample. The electronic image collection device is used to collect a first image of the sample, where the first image is defined by a plurality of pixels which together define a field of view. The first image is collected using an exposure duration of N seconds, where N is selected so that no pixel of the first image is saturated. A threshold intensity is then utilized to analyze the first image. The threshold intensity is selected so that at least some of the intensity values of the pixels of the first image exceed the threshold. Those pixels having an intensity measure that exceeds the threshold are identified and used to generate a mask.

The mask is a pixel-by-pixel representation of the field of view, which is at the same time, a pixel-by-pixel representation of the portion of the sample illuminated by light from the light source. Each pixel of the mask has a value of 0 if the pixel intensity reading exceeds the threshold and a value of 1 if the pixel intensity reading does not exceed the threshold. That mask is then used to create a structured illumination pattern of light to be used in the collection of a subsequent image. The intensity of each pixel of the light generated by the light source is set to 0 if the mask has a value of 0 at that pixel and to full illumination if the mask has a value of 1 at that pixel. That structured illumination pattern is then used to illuminate the sample and to collect a second image from the sample. The exposure duration for the collection of the second image is greater than that used for the collection of the first image. In some presently preferred implementations, the exposure duration is 2N seconds.

This process is then repeated until accurate intensity information is collected from the entirety of the sample. With each iteration, the exposure duration is increased (in some embodiments, the exposure duration is doubled) and the threshold is reapplied and new pixels that exceed the threshold are identified. Those pixels are added to the mask, which also contains the pixels identified in previously collected images to progressively shape the structured illumination pattern so that data are collected from portions of the image where signal intensity is weak. As subsequent images are collected, a complete and accurate measurement of signal intensity across the entire sample is obtained.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

Figure 1:
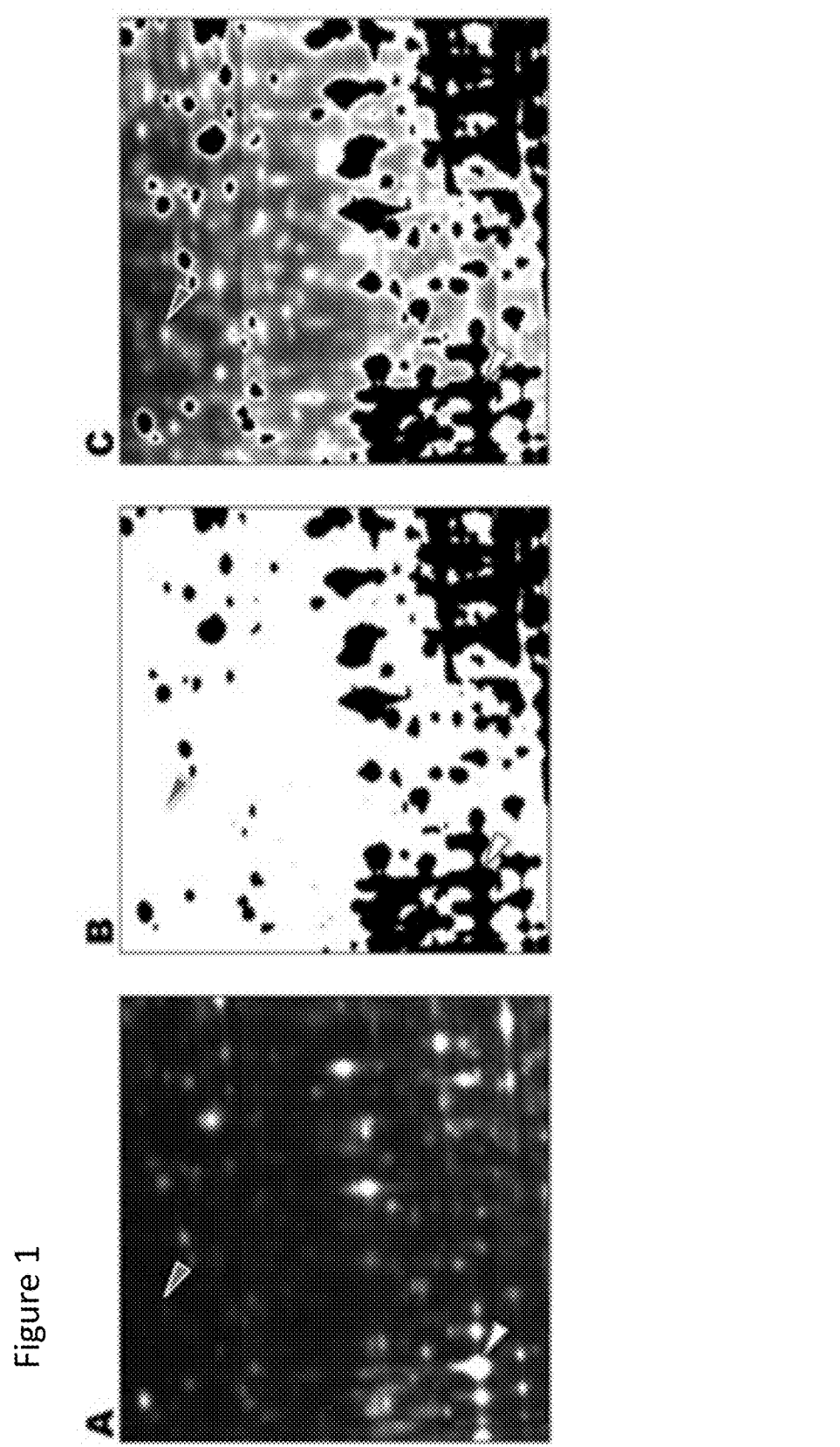
FIG. 1A shows a typical image of 2DE gel collected using prior art systems and methods.
FIG. 1B displays a binary mask generated from the image shown in FIG. 1A utilizing the systems and methods of the present invention.
FIG. 1C displays the binary mask shown in FIG. 1B overlaid onto an image of the same 2DE gel.

It is to be understood that the figures and descriptions of the present invention have been simplified to illustrate elements that are relevant for a clear understanding of the invention. The detailed description will be provided herein below with reference to the attached drawings.

The present invention provides a structured illumination (SI) imaging system for use in quantitative imaging that possesses improved dynamic range. As used herein, the phrase "structured illumination" refers to an illumination strategy in which different portions of the imaging area are illuminated with different amounts of light. In short, the systems of the present invention may be used to iteratively collect data from a visual field to achieve accurate measurements of signal intensity over a very large dynamic range. Initially, signal from high-intensity areas within a visual field is accurately measured by capturing short exposure time images from the sample using an image collection device. In some presently preferred implementations, the image collection device is a CCD camera, though one of skill in the art will recognize that numerous other types of imaging devices may be used, such as a photomultiplier tube coupled to a laser scanning head. As described further below, using those initial images, regions of the visual field containing high intensity signal are identified, and a binary mask is generated to block illumination of those high-intensity areas in subsequently captured images.

The exposure time used to collect subsequent images increases, thus increasing the amplitude of the signal from lower-intensity regions and permitting accurate measurement of their intensity. The increase of the exposure duration is set, in part, by the selection of the threshold value. For example, if the threshold is set to about half of the image detection device's maximum value, then the exposure duration is preferably doubled with each subsequent image. Similarly, if the threshold is set to one third of the image detection device's maximum value, then the exposure duration is preferably tripled with each subsequent image. Thus, as the threshold decreases relative to the image detection device's maximum value, the exposure duration utilized in collecting subsequent images is increased proportionately. In some presently preferred embodiments, the threshold is set to ½ of the CCD camera's maximum value and, thus, the exposure duration doubles between subsequent image collection.

After each image is collected, additional areas of the visual field where adequate signal has been measured are identified and added to the binary mask utilized during collection of the subsequent image. Through this iterative process, a wide range of signal intensities may be measured, while at the same time, avoiding saturation of any pixel within the field of view. The series of images may then be assembled into a single high-dynamic-range image that accurately and reliably reflects the range of signal intensity across the entire visual field. In some embodiments, these systems and methods of the present invention permit the detection of signal over a 1,000,000-fold intensity range.

A detailed description of certain preferred implementations of the present invention are provided below. These embodiments are described with reference to quantitative analysis of isolated protein in 2DE gels. While particularly well suited to application in that domain, the systems and methods of the present invention are equally useful in diverse settings, such as scene imaging, robotic vision, and digital microscopy (e.g., calcium imaging, immunohistochemistry) applications.

In one embodiment, a structured illumination (SI) system was developed where regions of a 2DE gel that contain high abundance proteins are "masked," while regions that contain low abundance proteins are fully illuminated. The central principle of the SI imaging systems of the present invention is the creation of a feedback loop between the imaging camera and a light source including, but not limited to, a video projector or laser scanning device. To initiate this feedback loop, an initial short exposure (N seconds: N is set so that no image pixels are saturated) of a gel is recorded using uniform, full-field illumination from the video projector. Any camera pixels registering a signal above a pre-determined threshold will be masked in subsequent exposures. In certain presently preferred embodiments, the threshold is 30,000 counts (just under half of the pixel saturation limit for a 16-bit camera). As used herein, a "masked" region of a visual field is a region that is not exposed to illumination.

Masking of those portions of the visual field is achieved by turning off (setting to black) all projector pixels within the masked region; the rest of the projector pixels are set to full illumination (white). Once a pixel is masked, it remains masked throughout the collection of subsequently captured images. The mask illumination pattern is projected onto the gel by the projector, and in some embodiments, as discussed above, an exposure of 2N duration is captured using the CCD camera. The new image provides signal intensity data from regions of the visual field that are of a lower intensity than those previously collected (and which are masked (and thus optically silent) during collection of the new image). That new image is used to generate the next masked image that is projected onto the gel and a 4N exposure is recorded. In some embodiments, this cycle is repeated 6-8 times, with a maximum exposure time of 64 seconds. The specific number of iterations and maximum exposure time may be established on a case-by-case basis, as determined by the properties of the particular sample being evaluated.

This selection of collection parameters and masking procedure ensures that none of the pixels in the series of SI images ever become saturated. By assembling intensity data from this sequence of masked images, the SI gel imager of the present invention achieves an improved dynamic range over conventional full-field illumination, single-exposure imagers. In some embodiments, the systems and methods of the present invention may achieve dynamic ranges of greater than 1,000,000 fold.

The masking strategy of the present invention is simulated in FIG. 1 using a typical 2DE gel image. FIG. 1A shows a fluorescent image of a typical 2DE protein gel collected using prior art systems and methods showing readily visible protein spots. Abundant proteins appear as bright spots (e.g., white arrowhead), while low-abundance proteins are not visible (e.g., gray arrowhead). Specifically, the white arrowhead is indicating the most abundant protein in the gel. According to the methods of the present invention, the intensity of signal from each pixel is measured. A preset intensity threshold is selected so that no individual pixel is saturated in an image collected using a relatively short exposure time. Typically, the intensity threshold is selected to be approximately half to approximately two-thirds of the CCD camera's measurable range. A binary mask can be generated by setting all pixels whose intensity exceeds the intensity threshold (30,000 in this example) to zero, represented as black, and unmasked pixels are set to one, shown as white (FIG. 1B). This mask is used to structure the illumination employed during collection of a subsequent image taken of the same gel. Further, the exposure time may be increased (e.g., doubled) between subsequent image collections without saturation of the high-intensity, but masked, regions of the visual field.

Here, the mask was applied onto the original gel through image-by-image multiplication. Through that manipulation, bright spots are masked (i.e., not collected in subsequently collected images) but many previously unseen, dim spots become visible, including the dimmest protein spot from the unmasked image (FIG. 1C).

If prior art methods were utilized in collecting and evaluating the image from FIG. 1A, a non-saturated image of the brightest spot (white arrowhead) with uniform field illumination limits the dim spot (gray arrowhead) to low dynamic range, rendering it effectively unmeasured. In contrast, the present invention permits the dimmest spots, such as the spot indicated by the gray arrowhead, to be boosted to high dynamic range by collecting a series of progressively masked images using extended exposure times. The progressive masking of already-measured regions of higher signal intensity thus permits an effective boosting of the signal from low-intensity regions of the image. As the series of progressively masked images are collected from the visual field, the systems and methods of the present invention permit an even sample of signal intensity space throughout the visual field.

Figure 2:
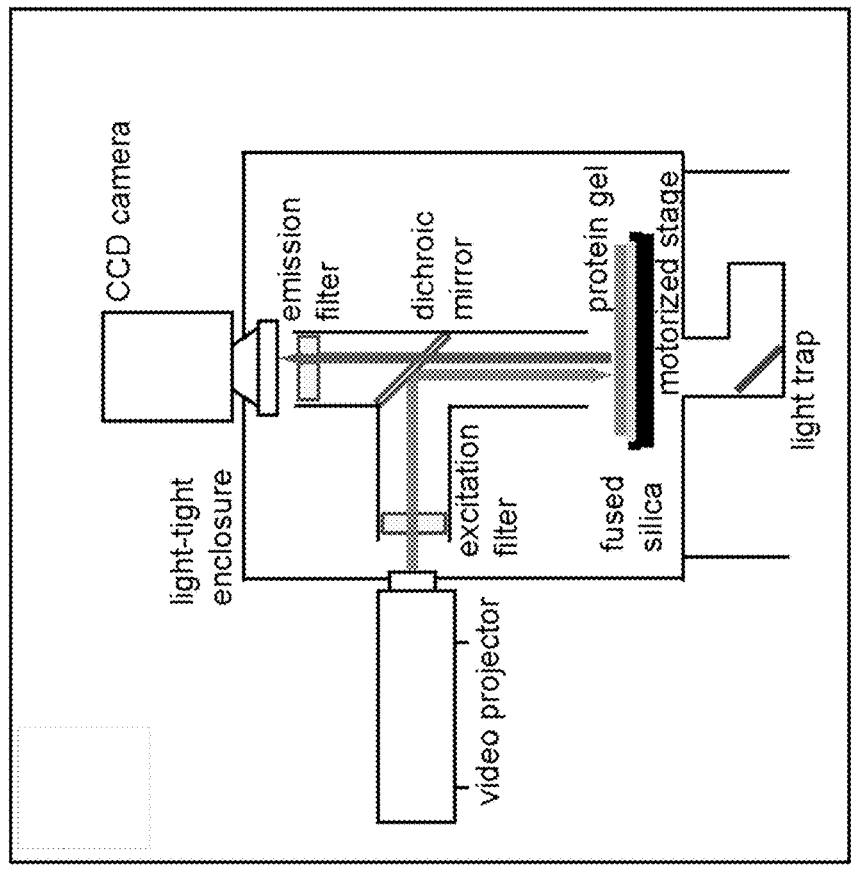
FIG. 2 shows a schematic of an implementation of the systems of the present invention.

Imaging systems of the present invention may be implemented in the following manner. The main components of an example embodiment of the SI gel imager are illustrated in FIG. 2A. An auditorium-grade LCD projector, with its standard lens removed, may be used as the light source. In other embodiments, the light source may be a scanning laser system. In some presently preferred embodiments, light emitted from the horizontally mounted video projector may be focused through a pair of achromatic lenses to project an image of the video projector's LCD array onto the gel (f=200 mm), then passed through fluorescence excitation bandpass filters mounted in a motorized filter wheel and redirected onto the gel via a multi-bandpass dichroic mirror mounted at 450°.

The gel may be placed in a black-anodized aluminum tray with a bottom plate made from a very low-fluorescence, fused-silica window to limit background light noise. To reduce back-reflected light, the fused-silica window may be broad-spectrum, anti-reflection coated (BBAR) glass. To further reduce stray light, excitation light that passed through the gel may be collected by an L-shaped light trap made of poly(methyl methacrylate) that was painted flat-black on the interior. Fluorescence emission from the fluorescently labeled proteins in the gel may pass back up through the dichroic beam splitter and matching emission band-pass filters mounted in a second, motorized filter wheel into the camera. In some embodiments, the entire light path was enclosed in 2"-diameter flat black optical tubing to limit stray light. Optical elements may be mounted on a three-axis stage and positioned with manual micrometers so that the appropriate field of view may be assessed. The light-tight, SI gel imager housing may be constructed from black anodized structural aluminum and black poly(methyl methacrylate) with the interior painted flat-black. One of ordinary skill in the art will recognize that multiple approaches and tools may be employed to reduce light noise, back-reflected light, and interference from other sources of stray light. The implementation here is present as an exemplary approach that was found to effectively reduce issues related to light-based noise.

In some embodiments of the systems of the present invention, the projector had a native resolution of 1024×768 pixels and a manufacturer-rated ANSI contrast ratio of 1:1000. One of ordinary skill in the art will recognize that any number of commonly employed light sources may be effectively utilized within the context of the present invention.

The systems of the present invention may also utilize a wide variety of devices for image collection. In some embodiments, an electronic CCD camera may be used, though one of skill in the art will also recognize numerous other high-quality image collection devices that are appropriate for use here. In the embodiment of the systems of the present invention utilized to collect the data discussed below, the camera was an actively cooled 16-bit scientific-grade CCD camera with a native resolution of 1300×1340 pixels. For the data disclosed here, the CCD camera's acquisition field was cropped to the central 1024×1024 pixels of the CCD and binned (4×4) to produce a 256×256 pixel image. These CCD adjustments ensure projector oversampling and increase signal-to-noise ratio of the camera image. The specific resolution of the image collection device and the binning employed for any given implementation may be varied to accommodate the operational constraints of the sample from which measurements are to be collected. For example, some samples may require a very high resolution to collected adequate data from all aspects of the visual field. One of ordinary skill in the art will be well positioned to select the appropriate image collection device (as well as its collection settings) when confronted with the particular implementation of interest.

To minimize projector spatial non-uniformity, the imaging systems of the present invention may be aligned so that the center of the projection area may be used for creating masks. Projector brightness and contrast settings are preferably set at intermediate values to minimize "clipping," a phenomenon where very bright and very dim projector pixels are not displayed due to excessive contrast.

The gel plate utilized to collect the data discussed below is able to accommodate 2DE gels up to 250×200 mm. The field-of-view of the CCD camera used here was 42×42 mm, which necessitated image tiling to completely capture large-format 2DE gel images, as discussed in the examples. The gel tray may be loaded onto an XY, motorized stage that provides two-axis movement relative to the camera's fixed field of view with 1 µm resolution. Again, these parameters and specific attributes of the components of the systems of the present invention may be varied to accommodate the specific sample and desired image collection resolution, as dictated by the particular task confronting the user.

The SI gel imager systems of the present invention may be controlled by a dedicated computer workstation via a purpose-built graphical software package that directs the imager's hardware components through, for example, serial port connections. The software package may execute the imager's main operations: namely, acquire images, generate image masks for the projector, direct stage movements for tiled acquisition, and perform rudimentary image operations such as zooming, intensity scaling, and animation of two-frame DIGE movies. The software package may also perform image registration and assemble the final high dynamic range images automatically after capture of the series of images.

The SI quantitative imaging system of the present invention is a new fluorescence imaging technology that significantly increases the dynamic range of protein detection in 2DE polyacrylamide gels upwards of 100-fold. By assembling intensity data from multiple exposures, the SI imager systems of the present invention provides for the detection of a 1,000,000-fold concentration range of fluorescently labeled protein in a single high-dynamic-range image. As discussed below, the SI quantitative image system's high dynamic range enabled the detection of the entire resolvable protein concentration range of Drosophila. These advances make the SI gel imager a very useful tool for investigating the proteomes of complex samples, identifying small changes including, but not limited to, protein abundance, mass and charge; changes that are often reflective of important physiologically relevant processes.

Certain specific aspects and embodiments of the present application will be explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

Example 1: Camera-Projector Image Registration

Accurately projecting masks onto gel spots preferably includes the steps of mapping every pixel of the projector image to its counterpart pixel in the camera field-of-view, a process called "image registration." Many image registration methods exist to satisfy different constraints on registration speed, accuracy, resistance to image noise and automation. Pixel-level alignment for the entire camera field-of-view is preferably employed with a relatively simple optical configuration (rigid planar camera and projector surfaces, monochromatic camera and projector images) and imaging requirements (static camera and projector positions, low acquisition speed, oversampled projector image, where the projector a larger pixel array than the camera's pixel array).

Figure 3:
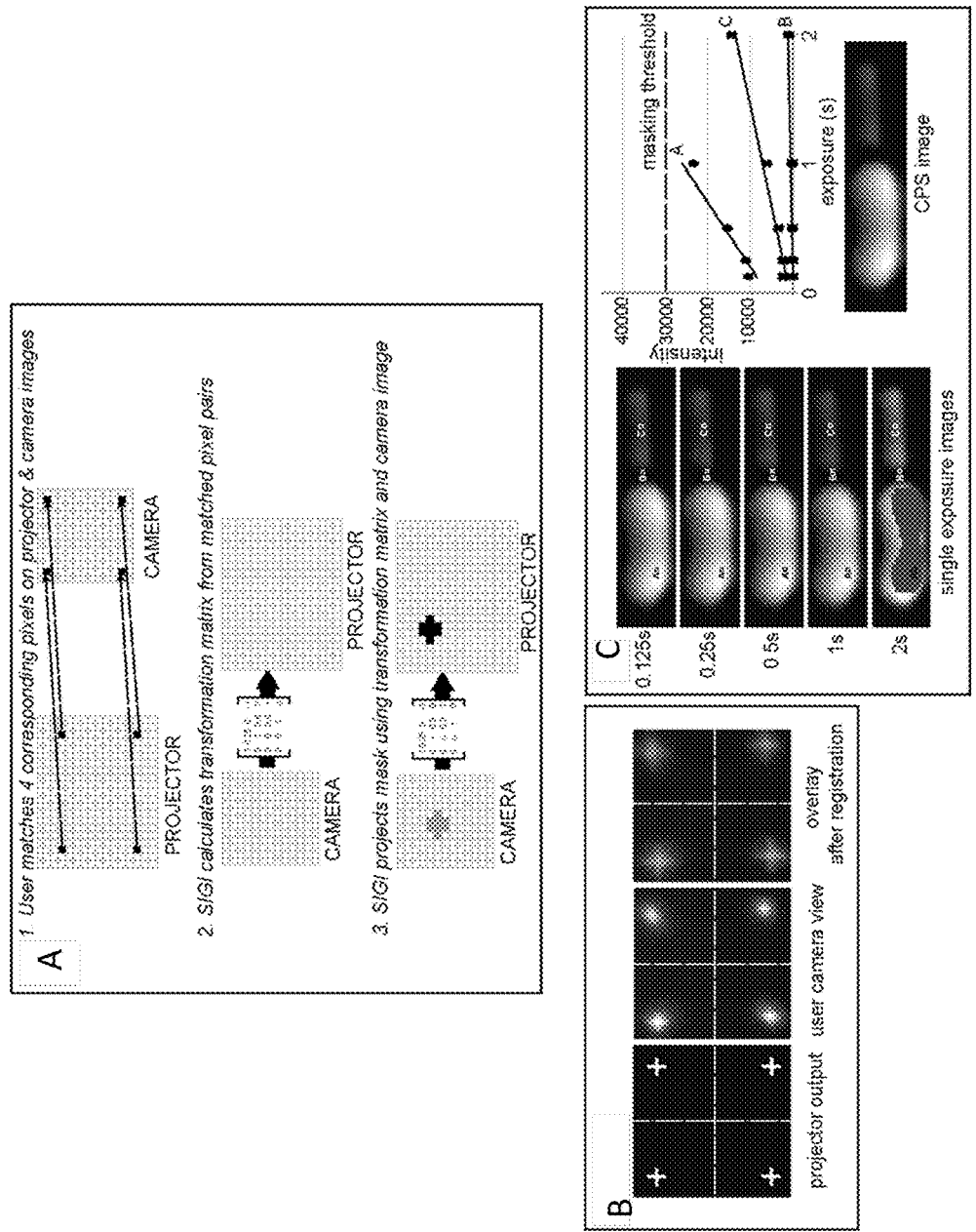
FIG. 3A depicts the workflow of image registration employed by the systems and methods of the present invention.
FIG. 3B displays the results of the image registration process employed by the present invention.
FIG. 3C shows an example of high dynamic range images obtained by the systems and methods of the present invention.

For the SI gel imager employed here, a control point matching method was chosen for supervised image registration, outlined in FIG. 3A. Briefly, the user selects corresponding pixels in camera and projector images, after which these coordinates are used to calculate a transformation matrix that is used to map camera pixels into the projector image plane.

In one example, the implementation includes: first, the projector casts images of crosses (5×5 pixel "+" signs) that are positioned at the four corners of the camera field-of-view onto a uniformly fluorescent target—a 1.5 mm thick, agarose slab gel containing Cy3-labeled protein (serum albumin) (FIG. 3B; left panel). An enlarged version of the resultant camera image is displayed on a customized piece of software (FIG. 3B; middle panel). The user then clicks on the center of each cross with the mouse cursor, which registers the corresponding coordinates for the projector image. A projective transformation matrix between the two sets of coordinates is calculated:

$$[CCD_x, CCD_y] = M^*[Proj_x, Proj_y],$$

where $Proj_x$ and $Proj_y$ are x- and y-coordinate of the projector pixels, $CCD_x$ and $CCD_y$ are x- and y-coordinates of the camera pixels and M is the matrix for a perspective transformation. The software package calculates M using the OpenCV software toolkit. OpenCV's getPerspectiveTransform( ) function takes $Proj_x$, $Proj_y$ from the projector image crosshair coordinates, $CCD_x$ and $CCD_y$ from the user clicks, and generates M explicitly. The camera image is then transformed using OpenCV's warpPerspective( ) function using M for the transformation parameters. The combined image of camera crosses overlaid on projector crosses is presented to the user for confirmation of image registration (FIG. 3B; right panel). Afterwards, the inverse matrix $M^{-1}$ is automatically used by the software package to project masks for all subsequent images. This supervised process makes image registration a highly robust process. Unsupervised methods were also tested, but performed poorly in the presence of slight defects in the target gel, while users can visually pick the crosses quickly and correctly regardless of minor target gel defects. Image registration may be performed infrequently, either when the projector or camera have been displaced for system maintenance or by minor vibrations during normal use. In one example embodiment, the software package undertakes image registration approximately every 15-20 gels, about once a month of typical use, with each registration session taking 1-2 minutes.

Example 2: Acquisition of High Dynamic Range Images by Present Invention

With image registration in place, the software package acquires a series of 16-bit images of a gel where the exposure time for each successive image is doubled. Initially, an image is collected using a short-duration exposure. All pixels within the image that exceed a user-set threshold (default=30,000 counts) are masked in all subsequent images of the SI series by turning the corresponding projector pixels to black, thus generating the mask. The mask is transformed to the projector coordinates as described above to shape the illumination pattern used in collecting the subsequent image. The exposure time is doubled and another image is acquired with the mask in place. With each subsequently collected image, new regions of the image that exceed the threshold are added to the ask, further shaping the illumination pattern.

Since CCD cameras have highly linear responses up to saturation and exposure times are known, it is possible to calculate the expected intensity of a masked pixel by modeling over the intensity values of unmasked exposures. The masking intensity threshold was set to 30,000 to minimize camera noise found at the extremes of the camera's detection limits. To compile this series of masked images into a single high dynamic range image, a linear response curve was calculated, expressed in counts per second (CPS) for all unmasked pixels. The software package applies to each pixel a least-squares linear regression of the form $$Y(c,t) = c_0 + c_1 t,$$

where Y is observed intensity in counts, t is exposure time in seconds; $c_0$ and $c_1$ are the best-fit offset and slope. Using the GNU Scientific Library mathematical toolkit, this interpolation is performed using the gsl_linear fit( ) function which takes integer arrays for Y and t and explicitly returns $c_0$ and $c_1$. The coefficient $c_1$, the slope term of the linear least-squares fit, represents the intensity response of a pixel. Goodness-of-fit was calculated for each pixel $$\% \varepsilon = \frac{\left(\sum_{i=1}^{n}\sqrt{\frac{(y-\hat{y})^{2}}{n}}\right) \times 100}{CPS},$$

where %ε is the pixel's percent residual, y is the observed intensity, ŷ is the interpolated intensity, n is the number of unsaturated exposures. The resultant SI image composed of $c_1$ coefficients for each pixel will be referred herein to as a CPS image.

To illustrate the CPS image calculation process, alcohol dehydrogenase (ADH) was labeled with Cy3-NHS dye using 10× the suggested concentration of minimal labeling dye to give Cy3-ADH, and 100 pg and 1 ng of this material was electrophoresed on a 12% SDS-PAGE gel. A series of 5 cycles of masked SI images were taken with 0.125 s, 0.250 s, 0.5 s, 1 s and 2 s exposures (FIG. 3C; left side of the panel). Three individual pixels were chosen to highlight. Pixel A is in the brightest part of the 1 ng Cy3-ADH band. With the masking threshold set at 30,000, pixel A was masked in the 2 s exposure, therefore its intensity in the 2 s image was not used in the CPS calculation.

Linear regression of the first four exposure values yielded a slope of 15,280 CPS. Dim pixels, such as pixel B, which contained no protein and pixel C, which was in the middle of the low-abundance Cy3-ADH band, were not masked since they never exceeded the masking threshold. All recorded intensity values for B and C were used to calculate CPS values of 526 and 6729, respectively. The first exposure of an SI series was typically set to 0.1 s, ensuring that even highly abundant protein spots had at least three unmasked exposures from which to calculate CPS values. Each subsequent exposure time was double the previous, balancing obtaining maximum image data with a reasonable imaging time. The same linear regression was used for all pixels in the image, generating a single CPS image from the original five single-exposure images. Within the context of the present examples, "CPS image" generally refers to images collected utilizing the systems and methods of the present invention.

A simple exemplary file format for CPS images was devised to streamline data storage and analysis. The header of the file records image dimensions and fluorophore wavelengths. The data portion stores CPS intensity values as 32-bit floating-point arrays, which is well beyond the dynamic range of current gel imagers. This raw image format is readily handled by common image analysis software packages, such as ImageJ.

Example 3: Post-Capture Image Processing

Since complete camera coverage of a typical 2DE gel requires 4×5 tiles (1024×1280 pixels), the software package utilized here performs automatic stitching after image acquisition to generate a single image that depicts the full gel (i.e., the relevant portion of the visual field). Previous work has determined a mathematical model for systematic variations in images of large format 2DE gels with an aim of eliminating them, particularly tiling artifacts. When applied to images collected using the systems and methods of the present invention, this model appears as:

$$\pi_{x,y} = (Y_{x,y} - \rho_{x,y})/\alpha_{x,y},$$

where π is the true abundance of proteins present in the gel, Y is the intensity of the observed image, ρ is the fluorescence emission of a blank polyacrylamide gel under uniform illumination, α is the fluorescence emission of a uniformly fluorescent (the bright-field image) gel target containing labeled proteins under the respective fluorescence filter, and x and y are pixel coordinates. To obtain ρ, we imaged an empty 12% polyacrylamide gel. For α, we prepared a uniformly fluorescent polyacrylamide gel: 1 µg of bovine serum albumin (BSA) was dissolved in the polyacrylamide gel solution before polymerization. To fluorescently tag the BSA within the gel with cysteine-reactive Cy3, the gel was then soaked in 40 mL of 1 mM tris(2-carboxyethyl)phosphine (TCEP) in a petri dish in the dark with shaking for 1 hour at 37° C. to reduce any disulfide bonds in the BSA, 4 µL of 10 mM Cy3-maleimide was then added and shaking continued for an additional hour. The uniform gel was then equilibrated in destain (40% methanol, 10% acetic acid) for 15 minutes and imaged.

To minimize artifacts from fluorescent dust particles or local inhomogeneities in the gel, the median image from nine 1-second exposures at slightly different XY positions relative to the camera field-of-view were used for the value of α. The image of true protein abundance t was then obtained computationally through ImageJ after image acquisition by solving the equation above.

Example 4: Evaluating Imager Detection Capability—Alcohol Dehydrogenase

To determine the practical dynamic range of the systems of the present invention, dilutions of purified protein samples were prepared in a typical SDS-PAGE mini-gel (which will be referred to as a 1D gel). A 10-fold dilution series of Cy3- and Cy5-labeled ADH was generated to create samples ranging from 10 µg to 10 pg of protein per lane. These samples were prepared from stock solutions where 240 µg of ADH was labeled with 10 nmol Cy3-NHS or Cy5-NHS dyes in 60 µl reactions, which represents a 10-fold increase in fluorescent labeling relative to the manufacturer's recommended minimal labeling. The stock solutions were diluted with an equal volume of 2× Laemmli sample buffer to a final concentration of 2 µg/l. To eliminate excess unbound dye, the samples were then centrifuged in a Centricon 10 kDa spin dialysis device at 4° C. and 5900 rpm for 90 minutes. The 10-fold serial dilution series was made by mixing 10 µl of sample with 90 µl of diluent (100 µl of diluent contained: 47.5 µl of 2× Laemmli buffer, 2.5 µl βME, 10 µl of unlabeled 10 mg/ml BSA as carrier protein and 40 µl H₂O). Bovine serum albumin (BSA) was added as a carrier to avoid protein loss due to adsorption, which is particularly important for the very low abundance samples.

All samples were then boiled for 2 minutes and 5 µl of each sample was loaded into consecutive lanes of a 12% polyacrylamide mini-gel in increasing concentration to minimize cross contamination from adjacent wells. Electrophoresis was performed at 130 V until the tracking dye front ran off the gel, approximately 90 minutes. These 1D gels were removed from their electrophoresis plates, placed on the fused silica window of the gel tray containing a covering layer of destain (50% methanol, 10% acetic acid), and imaged for 13 exposures with masking threshold set at 30,000 counts and first exposure time set at 0.01 s. The resultant CPS images were analyzed in ImageJ: a rectangular selection box was manually drawn around the central ADH band in each lane and the pixels contained within quantified. The same selection box size was used for the lanes containing 10 pg to 1 μg, while the box for the 10 μg lane was increased in size to accommodate the high amount of protein loaded in this lane.

Figure 4:
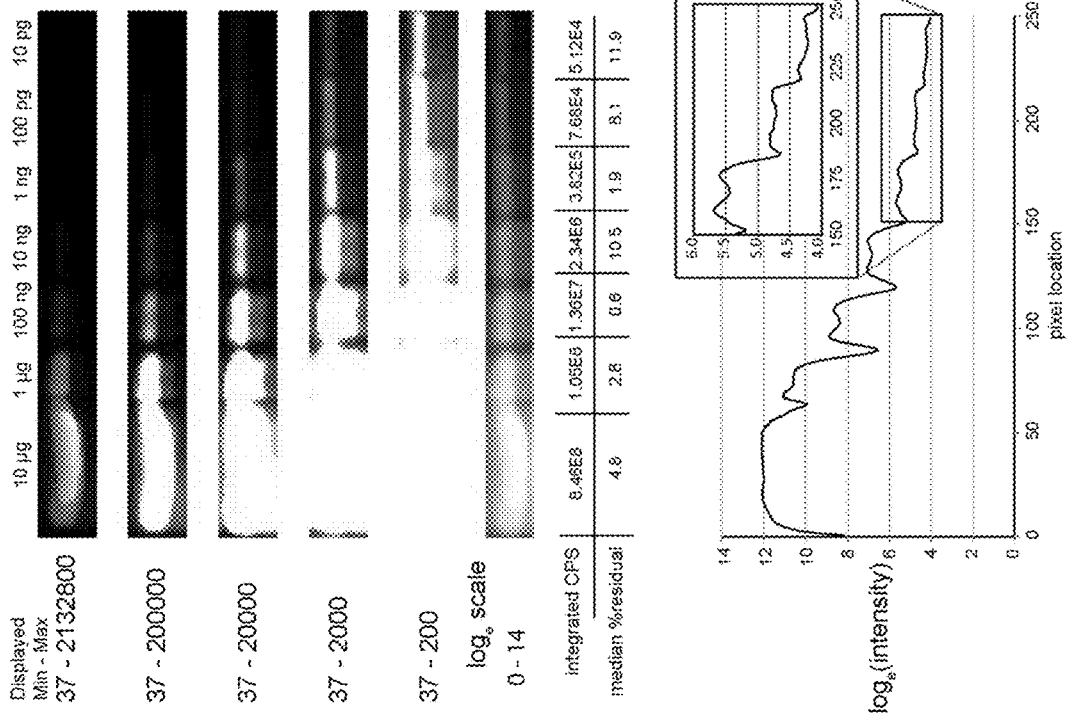
FIG. 4 provides an example of the present invention achieving a dynamic range of greater than 1,000,000 fold during measurement of protein concentration in a 1D gel.

The results of this experiment are shown in FIG. 4. To assess the detection range of the SI systems of the present invention, a CPS image of a 1D gel containing the ADH million-fold dilution series was acquired (FIG. 4). The CPS image was computed from a series of 13 progressively masked images where the exposures ranged from 0.01 to 40.96 s, and the masking threshold was set at 30,000 counts. Progressively decreasing the image's displayed maximum pixel intensity value (by masking relatively high intensity regions) according to the methods of the present invention permits measurement of the dim protein bands (FIG. 4; $1^{st}$-$5^{th}$ rows, minimal and maximal display values are shown to the left of each row). This high dynamic range CPS image demonstrates that the entire million-fold protein concentration range was detectable in a single image, which is not possible with prior art 16-bit image collection systems.

To visualize the full concentration range, the image is displayed using a natural logarithmic scale look-up table (FIG. 4; $6^{th}$ row). Horizontal line plots show that the samples form distinct bands of decreasing intensity from the lane containing 10 μg of protein down to the lane containing 10 pg (inset images). The image collected using the systems and methods of the present invention had a maximum intensity of 2.13 million counts, far exceeding the 65536 count upper limit allowed by single-exposure 16-bit images, as employed in the prior art. The integrated intensity of the 10 pg band was $5.12 \times 10^4$ CPS. The calculated median residual of the linear fit of this area, which represents the measurement error, was found to be 11.9%. A background region having the same area as the 10 pg band had an integrated intensity value of $2.62 \times 10^4$ CPS, with a median residual of 1.9%. Thus, the 10 pg band fluorescence was significantly brighter than the gel's background fluorescence. Similarly high dynamic range images were captured for Cy5-NHS-labeled ADH, indicating the SI gel imager performance is independent of the fluorophore used, allowing for the detection of low-abundance protein differences using DIGE labeling schemes (data not shown).

These experiments demonstrate that the SI gel imager of the present invention has an effective dynamic range of at least 1,000,000-fold in 1D gels loaded with 10×-labeled protein.

Example 5: Evaluating Imager Detection Capability—1×-Labeled Drosophila Embryo Extract To evaluate the performance of the systems and methods of the present invention with complex samples, large-format 2DE gels containing Drosophila embryo extract (DEE) were prepared: 100 μg of DEE (obtained as described previously in the literature) was labeled with 1 nmol of Cy3-NHS and incubated on ice for 20 minutes; 1 μl of quencher (5 M methylamine-HCl and 10 mM pH 8.0 HEPES) was added and the reactions were then incubated for 2 hours before being run on 18 cm 3-10NL IEF strips—this labeling extent will be referred to as 1×-labeled for 32,000 volt-hours. Second-dimension SDS-PAGE was done in 18×20 cm gradient gels (10-15% polyacrylamide), electrophoresed in Tris-Glycine-SDS running buffer at 300 volts until the tracking dye ran off the bottom of the gel (5-6 hours). Gels were then removed from running cassettes, equilibrated overnight in destain (50% methanol, 10% acetic acid) to proteins within the gel and imaged between fused silica plates the next day. For the 10×-labeled samples, 300 μg of DEE and 10 nmol of Cy3-NHS were used; the procedure employed was otherwise the same.

Two images of each DEE gel were obtained. First, a 32-bit CPS image generated from 12 structured-illumination exposures with masking threshold set at 30,000 counts and first exposure time set at 0.1 s was collected according to the methods of the present invention. Second, a single-exposure 16-bit TIFF image using a single 1 s full-field exposure was collected utilizing prior art methods. For quantitative analysis, the gels were cropped to the central 2×2 tiles (512×512 pixels) to eliminate artifacts such as streaks that commonly occur at the sides of the gels. Total image fluorescence (referred to as flux) was measured using ImageJ. Protein spots were detected and quantified using the DeCyder Differential Analysis 5.0 software suite (GE Healthcare), set to detect 400 spots in all gels. DeCyder employed a "watershed"-like detection method, segmenting the input image into patches containing pixels exceeding an internally calculated background value and returning the centroid of each patch. The 2DE DEE images were also analyzed using SourceExtractor (abbreviated as "SExtractor"), an open-source astronomy software package that detects point sources in dim images that we had used to analyze 2DE gels previously. Conceived as a galaxy counting tool, SExtractor subtracts background signal from input images to look for Gaussian point sources that satisfied oval shape constraints. Though fundamentally different in their approaches, both DeCyder and SExtractor showed similar trends in results. Data analysis was performed in Matlab and Excel.

The systems of the present invention were used to evaluate 2DE gels of DEE generated as disclosed above. The integrated fluorescence intensity of a region of the image, which could encompass a single protein spot, a set of protein spots, or large swaths of an image, will be referred to as the flux (borrowing the term from astronomy). Each image was processed to account for background fluorescence (darkfield correction) and to correct for variation in projector output across the imager field of view (bright-field correction). These correction elements yield images where the pixel values closely represent the fluorescent signal emanating from labeled protein, thus limiting artifacts arising from the imaging system.

Analysis of the 2DE gel images with DeCyder revealed advantages of images captured using the systems and methods of the present invention, compared to single-exposure images per prior art methods. Using standard parameters to assess proteins in the central 2×2 tiled region of a full 2DE gel (FIG. 5A), DeCyder detected an 8% (336/311) increase in raw spot count between the single-exposure image (prior art) and the CPS image (present invention). See Table 1. Since 2DE gels of fluorescent proteins tend to be noisy, unsupervised, raw spot counts by DeCyder tend to contain a significant fraction of falsely detected protein spots. All detected spots in the single-exposure and CPS images were visually inspected to validate the DeCyder spot detection. Visual inspection in the single-exposure image rejected 102 detected objects, reducing the number of detected spots by 33%. Visual validation of the CPS image resulted in the rejection of 53 putative protein spots, a 16% reduction (Table 1). Thus, about 50% fewer spots needed to be eliminated when analyzing the CPS image collected using the systems and methods of the present invention versus the prior art, single-exposure image.

This result indicates that the CPS images collected utilizing the systems and methods of the present invention were a more reliable input for DeCyder spot detection than images collected using prior art methods. In terms of visually verified spots, the CPS image contained 35.4% more detectable spots than the single-exposure image of the same 2DE gel, showing higher image quality for a more complete characterization of the protein sample (Table 1).

Figure 5:
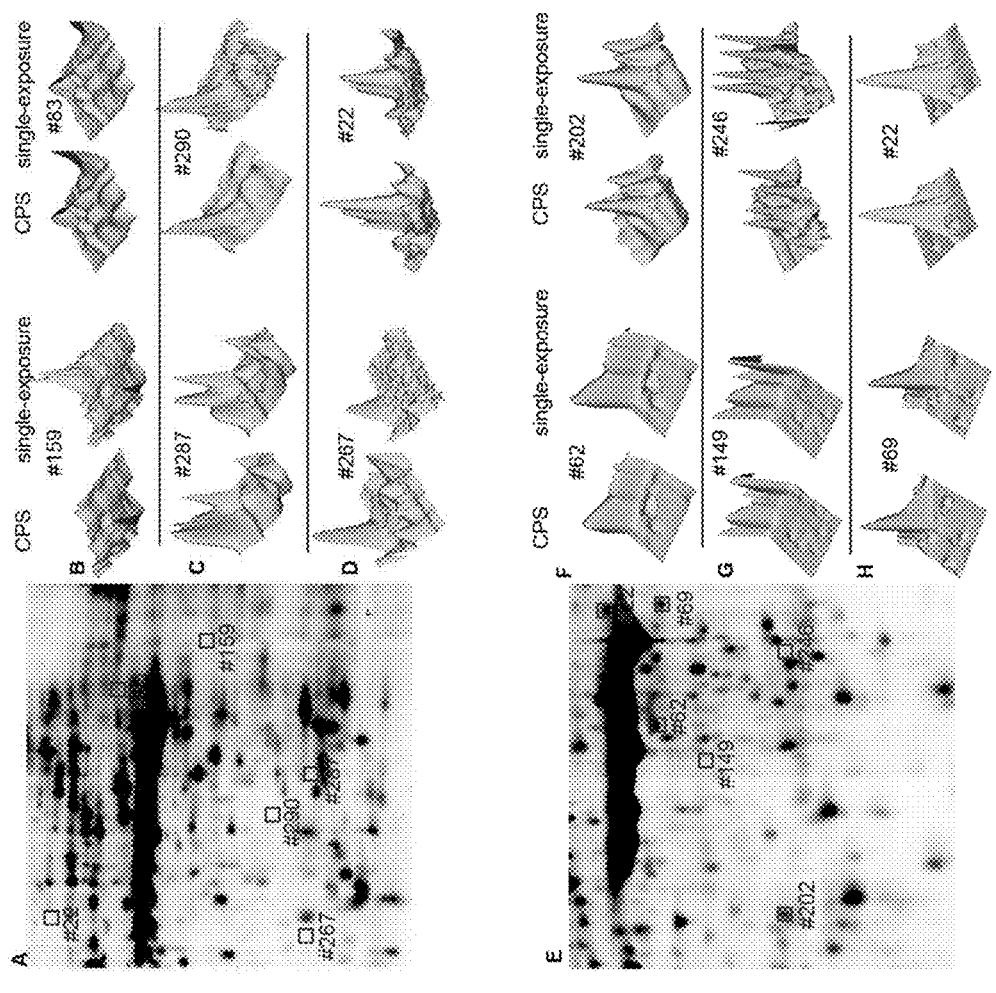
FIG. 5A displays an image of a 2DE gel of 1×-labeled *Drosophila* embryo extract collected using the systems and methods of the present invention.
FIGS. 5B, 5C, and 5D provide examples of intensity measurements of protein spots as numbered in FIG. 5A.
FIG. 5E displays an image of a 2DE gel of a 10×-labeled *Drosophila* embryo extract collected using the systems and methods of the present invention.
FIGS. 5F, 5G, and 5H provide examples of intensity measurements of protein spots as numbered in FIG. 5E.

To further illustrate the image quality differences between single-exposure and CPS images, the DeCyder's 3D Spot-View was used to display surface plots of spot features. This perspective allows one to visualize real spots, as well as those erroneously detected, in single-exposure versus CPS images (FIGS. 5 B-D). Since the CPS image collected utilizing the systems and methods of the present invention is a composite of multiple exposures, the resultant image is an averaged representation of the gel. The CPS image had lower noise in all parts of the gel, evident in its smoother contour plots. In some examples of dim spots, DeCyder was able to detect spots in the single-exposure image despite its higher noise (FIG. 5B). However, image noise caused DeCyder to falsely assign spots to the "shoulder" of an existing spot (FIG. 5C; left panel), or to background areas (FIG. 5C; right panel). Conversely, the same DeCyder analysis revealed genuine spots detected in the CPS image that were overwhelmed by noise and were consequently not detected in the single-exposure image (FIG. 5D; both panels).

TABLE 1

DeCyder spot detection and quantification of a 2DE gel containing 1X-labeled DEE.

|  | Single-exposure image | CPS image |
| --- | --- | --- |
| Number of detected protein spots | 311 | 336 |
| Number of verified protein spots | 209 | 283 |
| Dimmest protein spot (flux) | 12,100 | 2,360 |
| Brightest protein spot (flux) | 27,800,000 | 26,900,000 |
| Summed Yolk region (flux) | 102,000,000 | 90,100,000 |
| Flux ratio (Brightest/Dimmest) | 2,300 | 11,400 |
| Dynamic range (Summed Yolk/Dimmest) | 8,500 | 38,100 |

An important measure of the efficacy of the SI systems and methods of the present invention is to determine the dynamic range of cell extracts separated on 2DE gels. This was done by comparing the flux of the dimmest, verified protein spot relative to the flux of the brightest protein spot. The flux ratio for the single-exposure image was nearly 2,400, while the flux ratio for the CPS image was 12,000 (Table 1). Therefore, the dynamic range of 1×-labeled *Drosophila* embryo extract according to the CPS image was five-fold greater than the single-exposure image.

The most abundant protein in *Drosophila* embryos is the Yolk Protein. There are three closely related Yolk Proteins that share several common peptide sequences, each of which migrates as several post-translationally modified isoforms. The Yolk Proteins appear on 2DE gels as large series of very high abundance proteins. A previous study characterized the *Drosophila melanogaster* proteome using a LC MS/MS "shotgun proteomics" approach and reported a dynamic range of approximately 10,000-fold. "Comparative functional analysis of the *Caenorhabditis elegans* and *Drosophila melanogaster* proteomes." Schrimpf et al. *PLoS Biology* (2009). The high degree of Yolk Protein homology, which is 47-52% identity, means that these proteins share common tryptic peptides and that the different isoforms are indistinguishable by mass spectrometry. To compare dynamic range achieved by the systems and methods of the present invention with the LC MS/MS results, the maximum protein concentration was determined by summing DeCyder-reported fluorescence volumes for Yolk Protein spots in the gel images. Comparing the flux of dimmest protein spot to the summed Yolk Protein signal increased the dynamic range to 8,480 and 38,121 for the single-exposure and CPS images, respectively. This represents a nearly four-fold increase in dynamic range by the systems and methods of the present invention. It also indicates a four-fold improvement in detected protein concentration range in *Drosophila* embryo extract.

Example 6: Evaluating Imager Detection Capability—10×-Labeled *Drosophila* Embryo Extract In the preceding examples, it was demonstrated that 1×-labeled, purified proteins separated on 1DE gels only displayed a 10,000-fold dynamic range using CPS images, which is roughly consistent with the dynamic range observed in the 2DE gels of 1×-labeled *Drosophila* embryo extract. In order to achieve the desired million-fold detection range, the ADH protein samples were subjected to a 10-fold increase in labeling. To extend these findings, 10×-labeled *Drosophila* embryo extracts were separated by 2DE to determine if the SI gel imaging systems and methods of the present invention were able to detect protein across a 1,000,000-fold concentration range.

DeCyder spot extraction for a 10×-labeled 2DE gel of DEE showed a similar spot density and a modest 5% increase in verified spot count comparing the single-exposure to the CPS image of the present invention (Table 2). Increased labeling generated brighter fluorescent signal as expected, and DeCyder quantified more flux. For the single-exposure image, the dynamic range (flux ratio dimmest/brightest) for the 10×-labeled sample was similar to that of the 1×-labeled sample. Surprisingly, the dynamic range of the CPS image collected using the systems and methods of the present invention for the 10×-labeled sample was slightly lower than the single-exposure image of the same gel with the 10×-labeled sample. The same trend was also observed for the flux ratio of the summed yolk spots relative to the dimmest spot. It was expected to observe an increase in dynamic range when comparing 1×- to 10×-labeled DEE samples, based on the assumption that increased labeling would reveal more low abundance proteins.

Figure 6:
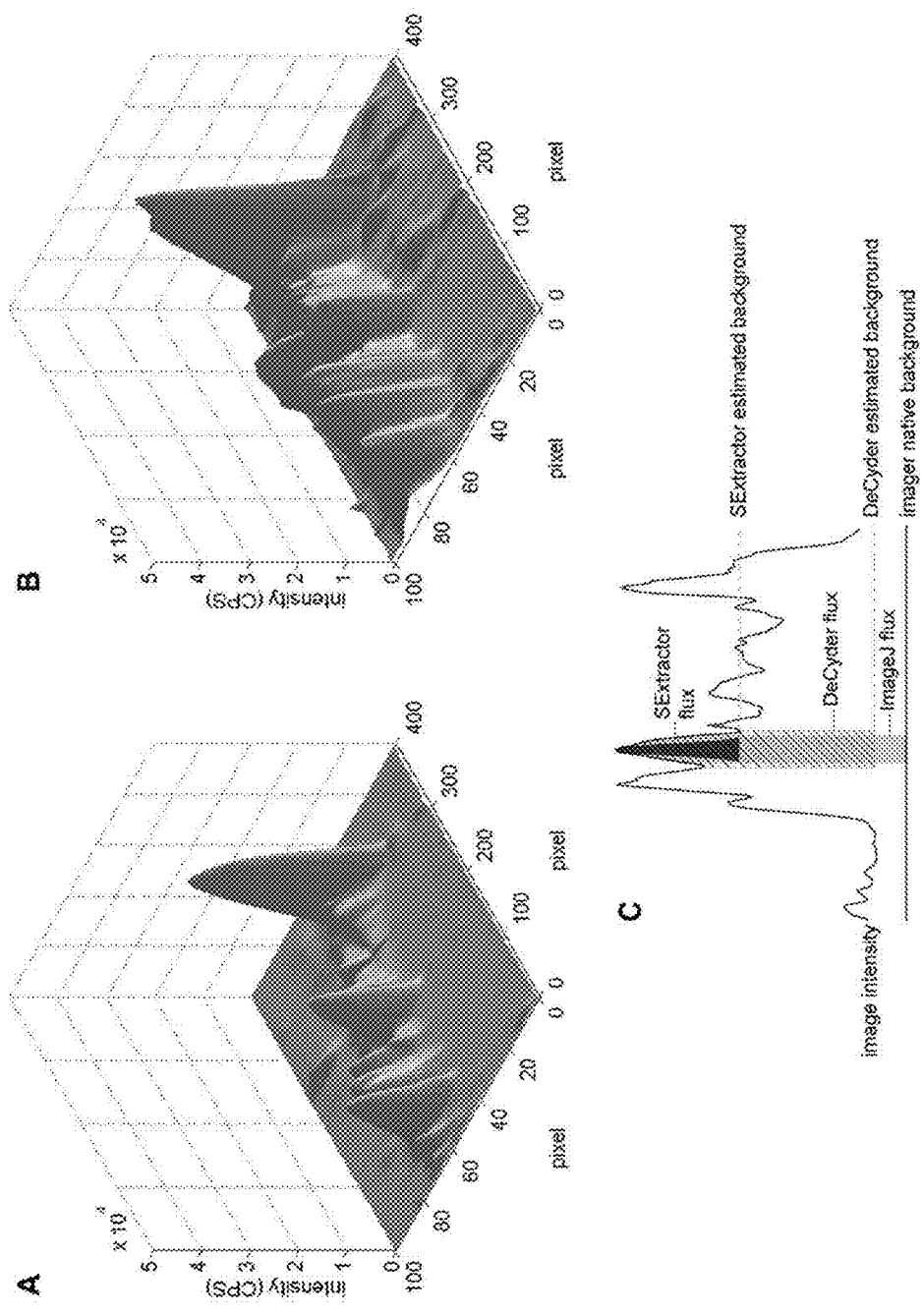
FIGS. 6A and 6B display surface plots of the Yolk Protein regions of a *Drosophila* embryo extract 2DE gel.
FIG. 6C shows an intensity cross-section of the Yolk Protein region of a *Drosophila* embryo extract, particularly illustrating flux estimates.

To further investigate this result, we examined the Yolk Protein area of the 10×-labeled DEE gel in greater detail. Despite the increase in fluorescence signal, the DeCyder measured flux emanating from the Yolk Protein spots did not increase 10-fold, as expected. Instead, when compared to the same area in 1×-labeled DEE 2DE gels, the 10×-labeled Yolk Proteins produced spots that were larger in cross-section (full width at half-maximum intensity), but not significantly higher in peak intensity. The 10×-labeled Yolk Proteins spots appear larger mostly in the second dimension, not the first dimension. The increased labeling reveals that these high-abundance proteins experience molecular crowding in the second dimension—i.e., they are forced to spread out further in this high percentage polyacrylamide gel because of molecular crowding in the gel matrix (FIG. 5). This molecular crowding may explain why the 10×-labeled Yolk Protein peaks did not have the expected Gaussian shape, but appeared to be somewhat plateaued (FIG. 6).

TABLE 2

DeCyder spot detection and quantification of a 2DE gel containing 10X-labeled DEE.

|  | Single-exposure image | CPS image |
|---|---|---|
| Number of detected protein spots | 326 | 318 |
| Number of verified protein spots | 279 | 293 |
| Dimmest protein spot (flux) | 10,400 | 18,100 |
| Brightest protein spot (flux) | 28,400,000 | 42,500,000 |
| Summed Yolk Protein region (flux) | 159,000,000 | 247,000,000 |
| Flux ratio (Brightest/Dimmest) | 2,750 | 2,350 |
| Dynamic range (Summed Yolk/Dimmest) | 15,420 | 13,700 |

Example 7: High-Abundance Protein Flux Measurement Errors

The discrepancy in flux ratio between 1x-labeled and 10x-labeled protein samples prompted further examination into how DeCyder quantified protein spots. Comparing the flux of the dimmest spot detected in the CPS image of the 1x-labeled DEE sample to the dimmest spot detected in the 10x-labeled DEE sample, showed an approximate 10-fold increase in flux, as expected. It is important to note that these were not the identical protein spots in the gels being compared, they were simply the lowest abundant spots detected (Table 1 versus Table 2). Comparing the brightest individual spot and the summed yolk region of the 1x-labeled and 10x-labeled samples revealed only a 1.6- to 2.7-fold flux increase, respectively (Table 1 versus Table 2).

While low abundance, well-separated protein spots roughly reflected the 10-fold increase in labeling extent, high abundance proteins failed to reflect the expected tenfold increase in labeling. In DeCyder, the background value for any spot segment is taken as the lowest 10th-percentile value of the spot border, not the gel's native background signal. This approximation works well for isolated dim spots, where the segment border is very close to the background signal. However, for bright protein spots in crowded regions of the gel, as is the case the Yolk Proteins, the spot background value is significantly higher than the native background value. Thus, the height of the protein spot is truncated, eliminating pixel counts between the segment border down to the image background, which can grossly underestimate the total flux from highly abundant protein spots.

To circumvent DeCyder's potential underestimation of high abundance proteins, the images were also analyzed by SExtractor, an astronomical image analysis package. Overall, the results from SExtractor were similar to DeCyder in terms of detected spots and flux ratios (Tables 3 and 4). However, SExtractor also suffered from an underestimation of high abundance proteins. SExtractor uses a mixed Gaussian fitting algorithm to detect celestial objects, which we adapted for 2DE gels. There are many different, user-controlled parameters that can impact spot-detection optimization, including spot size range, spot packing, and background estimation. However, one of the SExtractor's attributes that cannot be easily modified is the scope of background estimation. Inherent in the software is the assumption that all celestial objects are smaller than a pre-set size. Any detected object greater than this maximum object size is considered as a background source and its intensity contribution is removed. SExtractor produces a background image that is subtracted from the input image to yield a background-corrected image. The area occupied by very high abundance proteins exceeds the maximum object size limit of SExtractor such that part of the signal from very abundant proteins is considered background. Thus, SExtractor also underestimates the flux emanating from very high abundance proteins. In contrast to DeCyder which attempts to assign as much of the input image's area to spots as possible, SExtractor only quantifies areas that exceed its background threshold, further diminishing its dynamic range.

Figure 7:
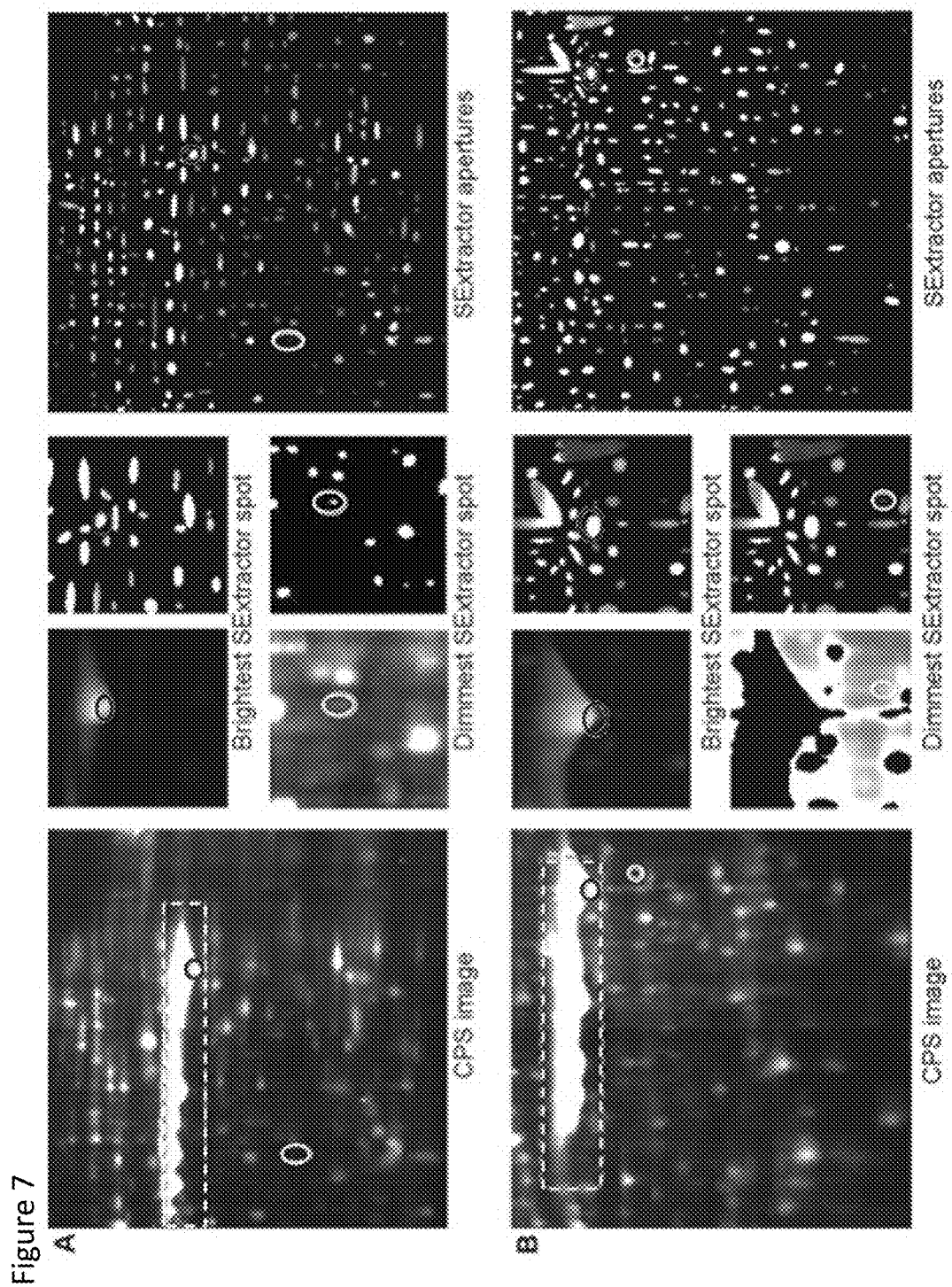
FIG. 7A illustrates an analysis of an image of a 2DE gel of 1×-labeled *Drosophila* embryo extract collected using the systems and methods of the present invention using SExtractor.
FIG. 7B illustrates an analysis of an image of a 2DE gel of 10×-labeled *Drosophila* embryo extract collected using the systems and methods of the present invention using SExtractor.

Examples of this effect are illustrated in FIG. 7: the brightest SExtractor spot comprised only a small fraction of the yolk spot (FIGS. 7A and B; the upper middle panels). The aperture highlighted by the black oval shows that only a small portion of the high-abundance Yolk Protein spot contributed to the flux measurement for this protein. This was also observed for both 1x- and 10x-labeled samples (FIGS. 9 and B). SExtractor also failed to detect very low abundance proteins as evidenced by the visual detection of many spots in the vicinity of the dimmest, SExtractor-detected spot that are less bright (FIG. 7A; lower middle panels-highlighted by the white oval). SExtractor was capable of detecting very-low abundance protein spot near very high abundance protein spots (FIG. 7B; lower middle panels—highlighted by the white oval). The CPS image was masked with a threshold of 45,000 CPS to display this very dim spot.

TABLE 3

SExtractor/ImageJ spot detection and quantification of a 2DE gel containing 1X-labeled DEE.

|  | Single-exposure image | CPS image |
|---|---|---|
| Number of verified protein spots | 272 | 301 |
| Dimmest protein spot (flux) | 1570 | 704 |
| Brightest protein spot (flux) | 1,460,000 | 2,670,000 |
| Summed Yolk spots (flux) | 29,100,000 | 55,200,000 |
| Flux ratio (Brightest/Dimmest) | 932 | 3,790 |
| Dynamic range (Summed Yolk spots/Dimmest) | 18,500 | 78,400 |

TABLE 4

SExtractor/ImageJ spot detection and quantification of a 2DE gel containing 10X-labeled DEE.

|  | Single-exposure image | CPS image |
|---|---|---|
| Number of verified protein spots | 293 | 326 |
| Dimmest protein spot (flux) | 1400 | 2380 |
| Brightest protein spot (flux) | 1,310,000 | 3,500,000 |
| Summed Yolk spots (flux) | 158,000,000 | 169,000,000 |
| Flux ratio (Brightest/Dimmest) | 942 | 1,470 |
| Dynamic range (Summed Yolk spots/Dimmest) | 113,000 | 71,100 |

Since SExtractor and DeCyder both underestimated the images' dynamic ranges, and other commercial 2DE spot analysis software packages suffer from similarly poor automated spot detection and quantification, ImageJ was used to manually draw a rectangular selection box around the Yolk Protein area (FIG. 7; dashed-line rectangles). Since all SI gel imager images are corrected for both background and bright-field variation, there is no need to reject any portion of a pixel's intensity after these imager-dependent corrections are applied. SExtractor generates a list of elliptical apertures, where each aperture represents a detected object. Each aperture is defined by its location, the length of the major and minor axes and the angle of the major axis. To estimate the total flux of an aperture, the aperture was superimposed on the corrected CPS image in ImageJ and the total pixel count was determined for all pixels within the aperture. Thus, the measured flux from a spot is the product of SExtractor detection and ImageJ quantification (shown as SExtractor/ImageJ flux in Tables 3 and 4).

The vast majority of protein within the Yolk Protein box is known to be Yolk Protein, therefore it is reasonable to perform a simple integration of the detected spots this region to estimate the total Yolk Protein flux using ImageJ. This approach yielded flux ratios for CPS images of 78,370 and 71,086 for 1×-labeled and 10×-labeled samples, respectively (Tables 3 and 4). These data demonstrate that allowing the image analysis tool to rely on systematically corrected images, without further background correction, produced very high dynamic range estimates that are roughly equal between the 1×-labeled and 10×-labeled samples. These data also suggest that increased labeling does not increase the detectable range of a sample. The systems and methods of the present invention are capable of detecting the full protein concentration range with the *Drosophila* embryo extract resolved on a 2DE gel. In other words, if SI imaging of 1×-labeled sample was not sufficient to detect the full concentration range of proteins in a sample, then 10×-labeling would be expected to reveal a wider concentration range. Since the detected protein concentration range was roughly similar between 1×- and 10×-labeling, one can assume the SI gel imaging systems and methods of the present invention detected the full range of proteins in these embryo extracts.

Example 8: Correction for Masking Boundary Artifact "Terracing"

Figure 8:
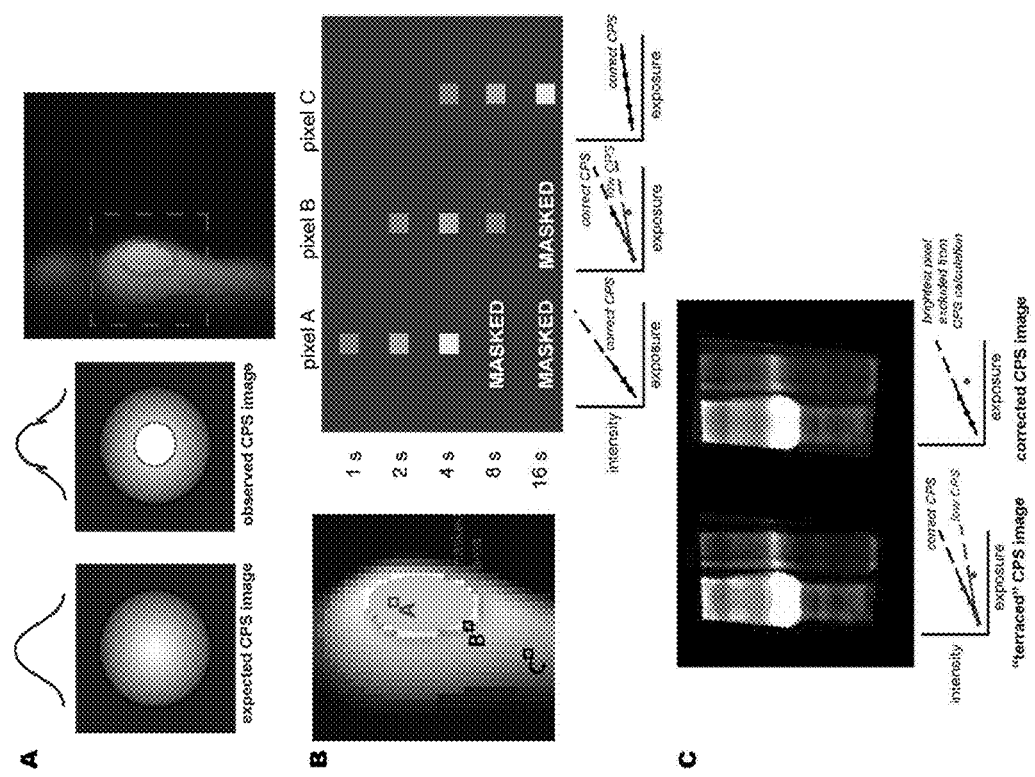
FIG. 8A displays an idealized labeled protein spot showing a characteristic Gaussian shape and a labeled protein spot showing a common artifact of encountered by application of the systems and methods of the present invention.
FIG. 8B shows an enlarged version of the image of FIG. 8A, including intensity data from five exposures from 1 second to 16 seconds.
FIG. 8C displays the image resulting from application of a correction of the artifact show in FIG. 8A.

During the course of developing the CPS image, a visual artifact in test images was sporadically encountered, as illustrated in FIG. 8. The artifact, here called "terracing," consisted of a ring of darkened pixels around very bright protein spots, disrupting the normally smooth Gaussian contours of these spots (FIG. 8; panel A). When the original pixel intensity values from the images that made up the CPS calculation were recovered, it became evident that these artifactual rings occur at the edge of the projected masks in the images.

Three different pixels in the terraced image were chosen to illustrate the problem in FIG. 8, panel B. Pixel A was within a bright area of the gel, and became masked after three exposures. Pixel A's CPS value is correctly interpolated from these three unmasked exposures. Similarly, pixel C was in a darker area of the gel, and its five unmasked exposures resulted in a correct CPS value. In contrast, pixel B contained reliable intensity values for the 1 s, 2 s, and 4 s exposures. However, in the 8 s exposure, several pixels surrounding pixel B were turned to black to generate the mask, and due to imperfect projector extinction, pixel B's intensity was partially diminished. Interpolating over the intensity values from 1 s, 2 s, 4 s, and the darkened 8 s exposure generated a lower CPS value for B than expected. This made pixel B appear dimmer than expected in the CPS image. Further, similarly located pixels at the edge of the masked area generated the darkened ring of pixel observed. These rings only appeared in images where there are highly abundant spots that require several levels of masking, and therefore the terracing problem occurred only sporadically.

A correction for the terracing artifact was developed. The CPS image is calculated at the end of the image acquisition process: the software package assembles a vector of exposure time values and a vector of intensity values. To ensure only reliable intensity values are used in the CPS calculation, a check condition in the software package source code was added to require that each intensity value is greater than twice the previous value, that is, $Y_{n+1} > 2*Y_n$. This check is based upon the facts that (1) doubling exposure times during acquisition should, at the least, double signal intensity; and (2) the CCD camera utilized as part of the system of the present invention has very linear response. If that condition is not met, the exposure time and intensity value vectors are truncated to only include values that met the check. It was demonstrated that application of this conditional check robustly corrected the terracing problem (as illustrated in FIG. 8 (panel C) using a 1D gel), while maintaining the accuracy of the CPS calculations.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A method of generating an image that accurately captures signal intensity of a sample, comprising the steps of:
    a) illuminating the sample with light generated by a light source, wherein the light generated by the light source is capable of being controlled on a pixel-by-pixel basis;
    b) collecting a first image of the sample using an electronic image collection device to collect light from the sample, wherein the first image comprises a plurality of pixels that together define a field of view, further wherein the first image is collected using an exposure duration of N seconds, wherein N is selected so no pixel of the first image is saturated by the light from the sample;
    c) selecting a threshold intensity, wherein the threshold intensity is selected so that the intensity of at least some of the plurality of pixels of the first image exceed the threshold;
    d) identifying which pixels in the first image have an intensity reading that exceeds the threshold;
    e) generating a first mask that is a pixel-by-pixel representation of the field of view, wherein each pixel of the first mask has a value of 0 if the pixel intensity reading exceeds the threshold and wherein each pixel of the first mask has a value of 1 if the pixel intensity reading does not exceed the threshold;
    f) using the first mask to generate a structured illumination pattern of light, wherein an intensity of each pixel of the light generated by the light source is set to 0 if the first mask has a value of 0 at that pixel and to full illumination if the first mask has a value of 1 at that pixel;

g) collecting a second image from the sample using the structured illumination pattern of light generated by the light source using an exposure duration of greater than N seconds;

h) identifying which pixels in the second image have an intensity reading that exceeds the threshold;

i) generating a second mask that is a pixel-by-pixel representation of the field of view, wherein each pixel of the second mask has a value of 0 if the pixel intensity reading exceeds the threshold and wherein each pixel of the second mask has a value of 1 if the pixel intensity reading does not exceed the threshold, further wherein a pixel of the second mask will have a value of 0 if that pixel had a value of 0 in the first mask;

j) using the second mask to generate a second structured illumination pattern of light, wherein an intensity of each pixel of the light generated by the light source is set to 0 if the second mask has a value of 0 at that pixel and to full illumination if the second mask has a value of 1 at that pixel; and k) collecting a third image from the sample using the second structured illumination pattern of light generated by the light source using an exposure duration of greater than that used to collect the second image.

2. The method of claim 1, further comprising the steps of repeating steps h) through k) to generate a series of images that together contain accurate intensity information from the entirety of the sample.

3. The method of claim 2, wherein the accurate intensity information reflects a 1,000,000-fold dynamic range.

4. The method of claim 1, wherein the sample is a biological sample.

5. The method of claim 4, wherein the biological sample is a 2-dimensional or 1-dimensional electrophoresis gel with proteins embedded therein.

6. The method of claim 5, wherein the proteins are labeled with a fluorescent marker.

7. The method of claim 6, wherein the light has a wavelength capable of exciting the fluorescent marker.

8. The method of claim 1, wherein the light source is a LCD projector or a scanning laser illumination system.

9. The method of claim 1, wherein the electronic image collection device is a CCD camera or a photomultiplier tube coupled to a laser scanning head.

10. The method of claim 1, wherein the threshold is set to ½ of a maximum intensity measurement of the electronic image collection device.

11. The method of claim 10, wherein the exposure duration used to capture the second image is 2N.

12. The method of claim 11, wherein the exposure duration used to capture the third image is 4N.

13. The method of claim 10, wherein the exposure duration is increased by a factor of two for the collection of each subsequent image.

14. A system for accurately capturing signal intensity of a sample, comprising:

a light source capable of being controlled on a pixel-by-pixel basis;

an electronic image collection device used to collect light from the sample using an exposure duration of N seconds and generate an image of the sample, wherein the image comprises a plurality of pixels, wherein no pixel of the image is saturated by light from the sample; and a computer system adapted to control the light source and the electronic image collection device, wherein the computer system includes a software package capable of applying a threshold to the image to identify which pixels in the image have an intensity reading that exceeds the threshold and generating a mask based on that threshold, wherein each pixel of the mask has a value of 0 if the pixel intensity reading exceeds the threshold and wherein each pixel of the mask has a value of 1 if the pixel intensity reading does not exceed the threshold;

wherein the software package uses the mask to generate a structured illumination pattern of light and wherein the software package sends that structured illumination pattern to the light source, wherein the structured illumination pattern of light includes an intensity of each pixel of the light generated by the light source set to 0 if the mask has a value of 0 at that pixel and to full illumination if the mask has a value of 1 at that pixel; and wherein the light source uses the structured illumination pattern of light to illuminate the sample for the collection of a second image using an exposure duration of greater than N seconds.

15. The system of claim 14, wherein the system is capable of performing the steps iteratively to generate a series of images that together contain accurate intensity information from the entirety of the sample.

16. The system of 15, wherein the accurate intensity information reflects a 1,000,000-fold dynamic range.

17. The system of claim 14, wherein the biological sample is a 2-dimensional or 1-dimensional electrophoresis gel with fluorescently labeled proteins embedded therein.

18. The system of claim 17, wherein the light has a wavelength capable of exciting the fluorescent label.

19. The system of claim 14, wherein the light source is a LCD projector or a scanning laser illumination system.

20. The system of claim 14, wherein the electronic image collection device is a CCD camera or a photomultiplier tube coupled to a laser scanning head.

* * * * *